United States Patent [19]

McConnell et al.

[11] Patent Number: 4,976,326

[45] Date of Patent: Dec. 11, 1990

[54] WEIGHING SYSTEM

[75] Inventors: Bain C. McConnell; William R. Jarvis, both of Winston-Salem; C. Fred Demey, III, Belews Creek; James G. Maddrey, Jr., Walkertown, all of N.C.

[73] Assignee: R. J. Reynolds Tobacco Company, Winston-Salem, N.C.

[21] Appl. No.: 455,045

[22] Filed: Dec. 22, 1989

[51] Int. Cl.⁵ ............................................. G01G 19/00
[52] U.S. Cl. .......................................... 177/145; 177/1
[58] Field of Search ...................................... 177/1, 145

[56] References Cited

U.S. PATENT DOCUMENTS

| | | | |
|---|---|---|---|
| 3,225,847 | 12/1965 | Vergobbi | 177/52 |
| 3,433,054 | 3/1969 | Mutter | 73/28 |
| 3,901,334 | 8/1975 | Rose | 177/52 |
| 4,010,595 | 3/1977 | Boyd | 53/55 |
| 4,195,736 | 4/1980 | Loeffler | 177/188 X |
| 4,405,023 | 9/1983 | Guardiola | 177/145 X |
| 4,564,103 | 1/1986 | Sashiki et al. | 177/25.18 X |
| 4,609,058 | 9/1986 | Sashiki et al. | 177/1 |
| 4,817,744 | 4/1989 | Power, Jr. | 177/145 |

*Primary Examiner*—George H. Miller, Jr.
*Attorney, Agent, or Firm*—Grover M. Myers

[57] ABSTRACT

The system includes a linear array of mutually spaced weighing devices. Each weighing device has a weighing platform having an article-receiving seat and a sloping cam surface for directing articles onto such seat. During each weighing operation, a group of articles to be weighed are moved in unison with each other to successive different locations longitudinally of the array of weighing devices. In each of the locations a plurality but less than all of the articles are weighed substantially simultaneously by associated underlying ones of the weighing devices. Articles weighed at each location are separated from each other by other articles that are not weighed at such location. An article support member supports the articles for movement longitudinally of the array of weighing devices, and also for limited vertical movement relative to the support member. Relative vertical movement between the support member and an article supported thereby occurs as the article's longitudinal movement brings it into and out of engagement with the sloping cam surface of the weighing platform of one of the weighing devices. Upward movement of the article raises it to the elevation of the article-receiving seat of the weighing platform. The weighing devices are enclosed within a substantially draft-free housing. A control mechanism controls longitudinal movement of the articles relative to the weighing devices, and automatically records the weights of the articles. The articles weighed may be Cambridge units used in ascertaining the "FTC tar" content of cigarettes.

30 Claims, 4 Drawing Sheets

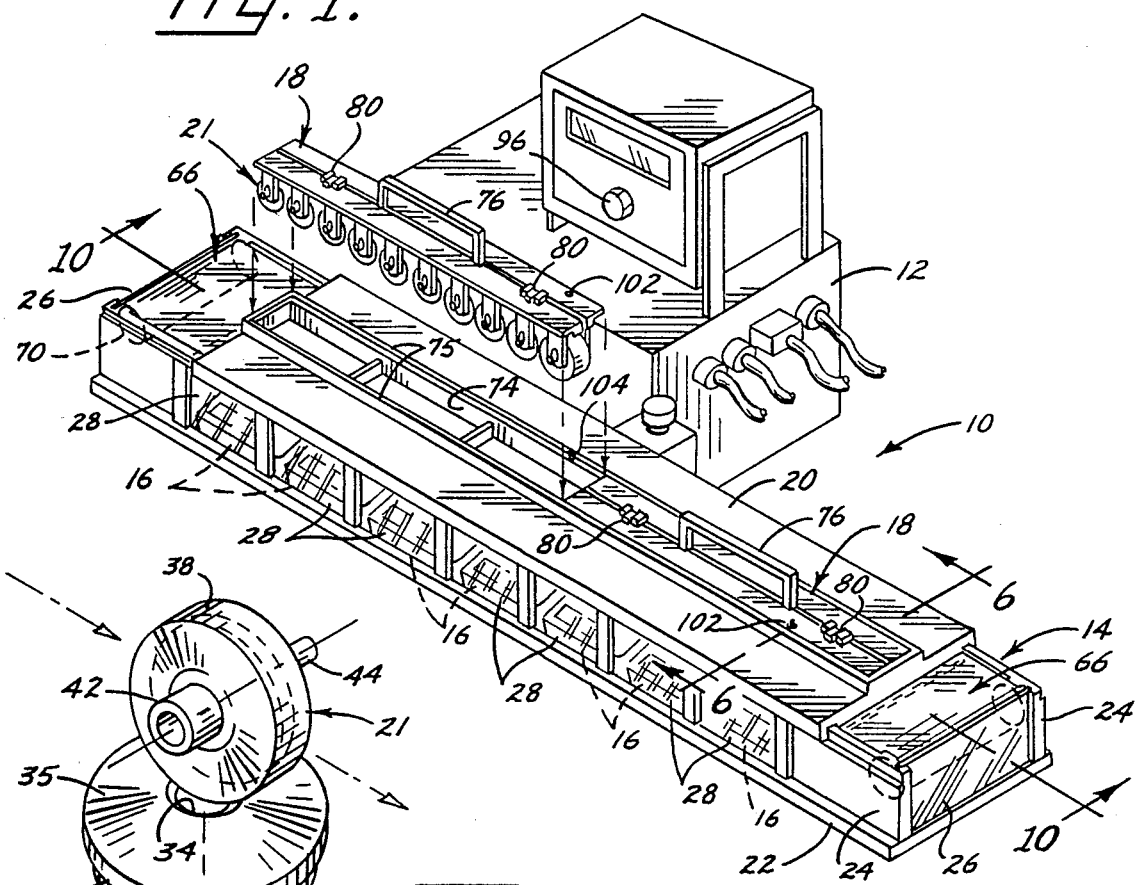
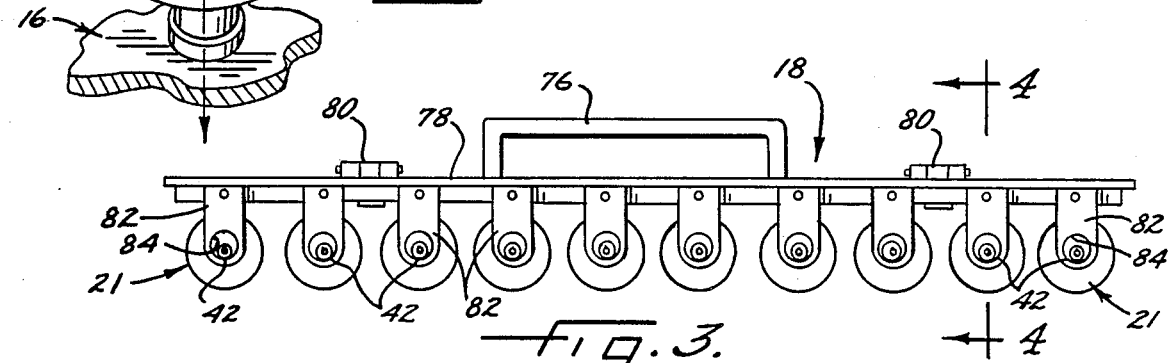
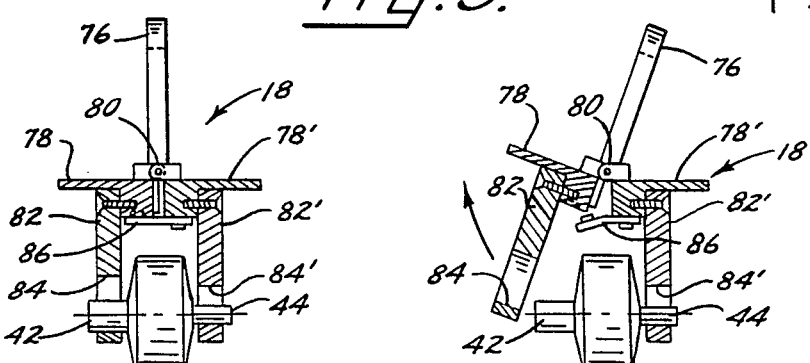
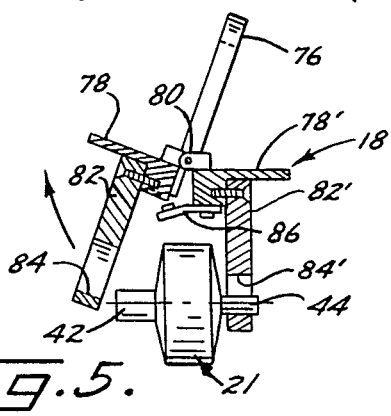

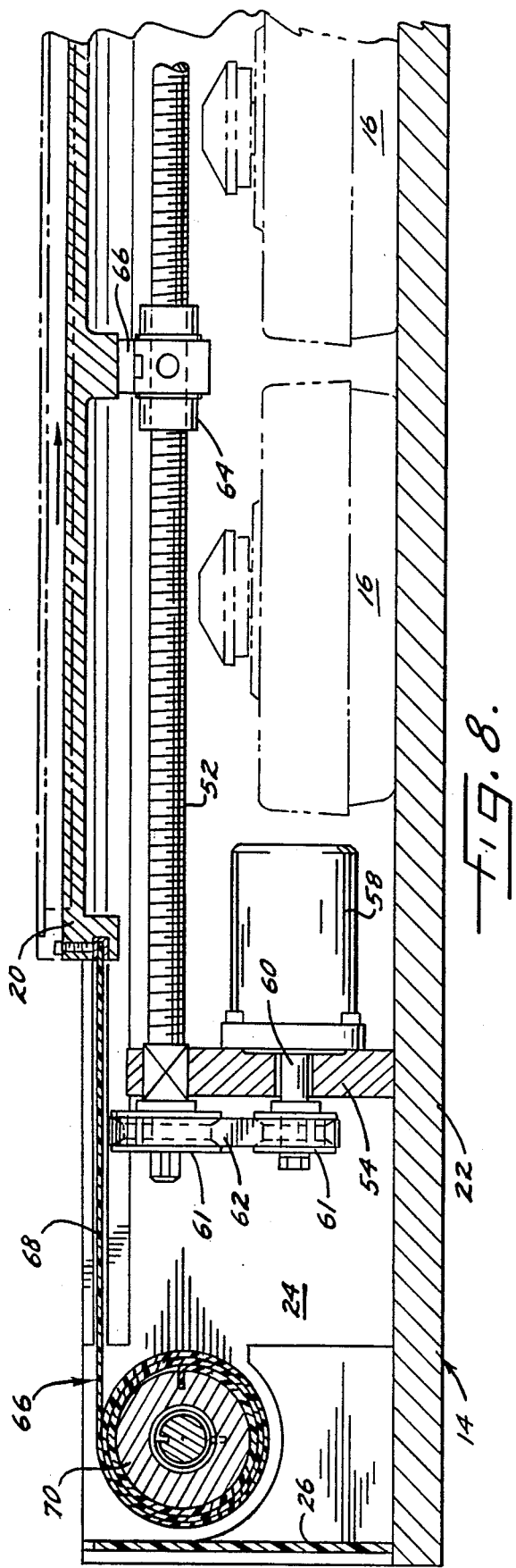
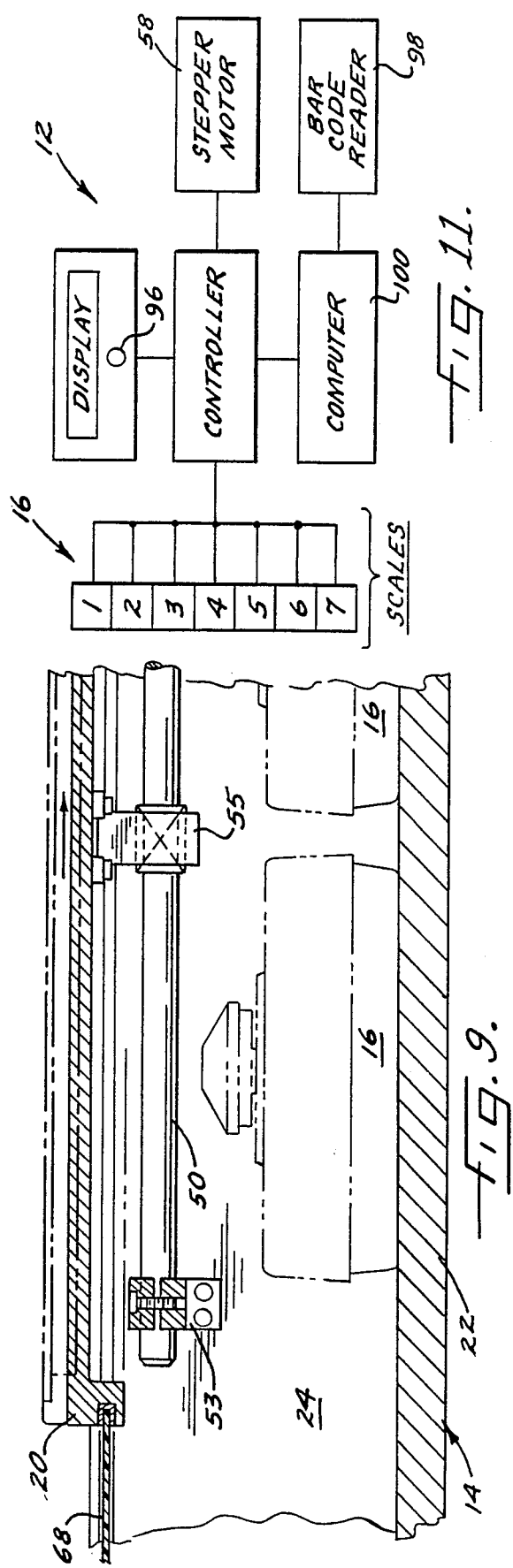

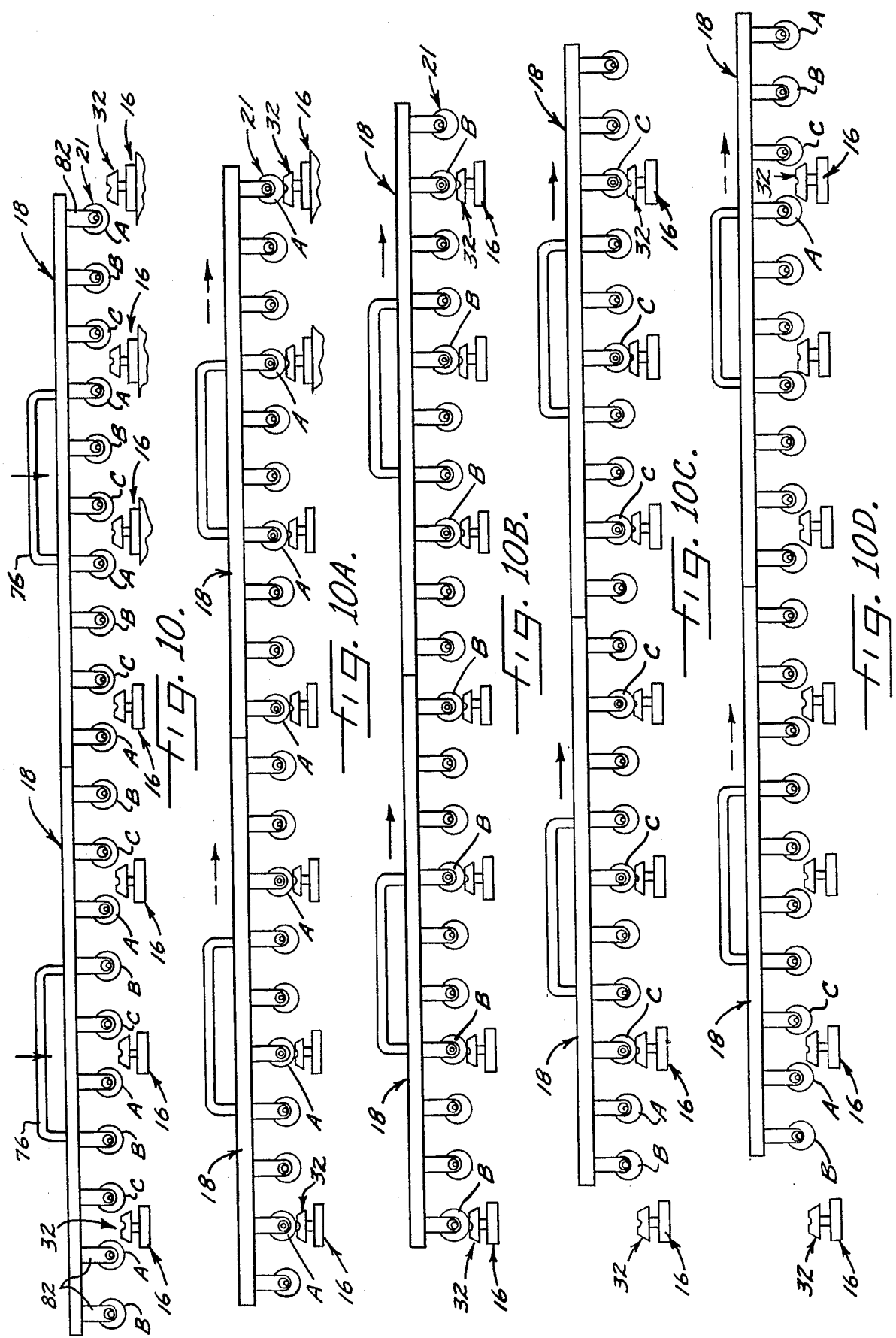

WEIGHING SYSTEM

FIELD OF THE INVENTION

This invention relates to systems for weighing articles, particularly (but not necessarily exclusively) Cambridge filter units used in automatic smoking machines to determine the "FTC tar" content of cigarettes.

BACKGROUND OF THE INVENTION

In order to comply with various governmental regulations, cigarette companies regularly test cigarettes in an automatic smoking machine that typically smokes twenty cigarettes simultaneously. The cigarettes are supported in the smoking machine by Cambridge filter units, each of which consists of a disc-shaped body containing a filter pad and having tubular stems extending forwardly and rearwardly from its opposite sides. A cigarette to be tested is inserted into one of these stems. The other stem is connected to a controlled vacuum source which causes air to be periodically drawn through the cigarette and the Cambridge unit as the cigarette is smoked by the machine. The smoke passes through the filter pad of the unit, and so-called "FTC tar" and moisture are retained by the pad. The entire unit is removed from the smoking machine and weighed after the cigarette has been smoked to a preselected extent. This weight is then compared to the weight of the unit prior to use thereof, to determine the "FTC tar" content of the cigarette.

Weighing of the Cambridge units, both before and after use thereof in smoking machines, is customarily now accomplished by technicians who manually place each unit upon a top-loading balance, record its weight, and then remove the pad from the balance. During a typical day over 600 individual weighings may be made in this manner. The foregoing technique for determining and recording the weight of the Cambridge units is highly inefficient, monotonous, tedious and error-prone, as a consequence of which it is unsatisfactory from the viewpoint of cost, accuracy of results and personnel satisfaction.

DESCRIPTION OF THE PRIOR ART

U.S. Pat. No. 3,433,054 discloses a cigarette smoking machine and Cambridge pad units used therein. The following additional U.S. patents disclose weighing machines or systems that may be of interest relative to the present invention: 3,225,847, 4,010,595 and 4,609,058.

SUMMARY OF THE INVENTION

The present invention provides an improved method and apparatus for efficiently, rapidly and accurately determining and recording the weight of Cambridge units or similar articles.

The apparatus of the invention includes a plurality of weighing devices that are located in spaced adjacent relationship to each other and define an array. The apparatus further includes article transporting means for transporting a plurality of the articles to be weighed in unison with each other generally parallel to the array of weighing devices between successive different locations at each of which different ones but not all of the transported devices are engaged, supported and weighed by underlying associated ones of the weighing devices.

The method of the invention includes the steps of providing an array of laterally spaced weighing devices, and transporting a plurality of articles to be weighed relative to the array in substantial unison with each other to successive different locations at each of which different ones of the articles are engaged, supported and weighed by underlying ones of the weighing devices.

When the articles to be weighed are Cambridge units, the transporting means preferably includes article support means by which a plurality of such units are simultaneously transported as a group to the weighing apparatus, and movable carriage means that receives the support means and effects movement of the support means and Cambridge units to the different locations relative to the array of weighing devices. The support means constrains the units for movement with the carriage means parallel to the array, while permitting limited vertical movement of the units onto and from the weighing pans or platforms of the weighing devices.

DESCRIPTION OF THE DRAWINGS

Other features of the invention will be apparent from the following description of illustrative embodiments thereof, which should be read in conjunction with the accompanying drawings, in which:

FIG. 1 is a partially exploded top front perspective view of a weighing apparatus in accordance with the invention;

FIG. 2 is an enlarged top perspective view of a Cambridge unit and of an underlying weighing platform of one of the weighing devices of the apparatus;

FIG. 3 is an enlarged side elevational view of a support member for transporting a group of Cambridge units to and longitudinally of the apparatus;

FIG. 4 is an enlarged vertical sectional view taken substantially along the line 4—4 through the support member of FIG. 3;

FIG. 5 is a view similar to FIG. 4, but showing hinged components of the support member in another relative position;

FIG. 8 is a fragmentary longitudinal sectional view taken substantially along the line 8—8 of FIG. 6;

FIG. 9 is a fragmentary longitudinal sectional view taken substantially along the line 9—9 of FIG. 6;

FIGS. 10, 10A, 10B, 10C, and 10D are partially schematic illustrations taken generally along the line 10—10 of FIG. 1, showing movements undergone by the Cambridge units relative to the array of weighing devices during operation of the apparatus; and FIG. 11 is a diagrammatic representation of control and recording components of the apparatus.

DESCRIPTION OF THE PREFERRED EMBODIMENTS

Figure 6:
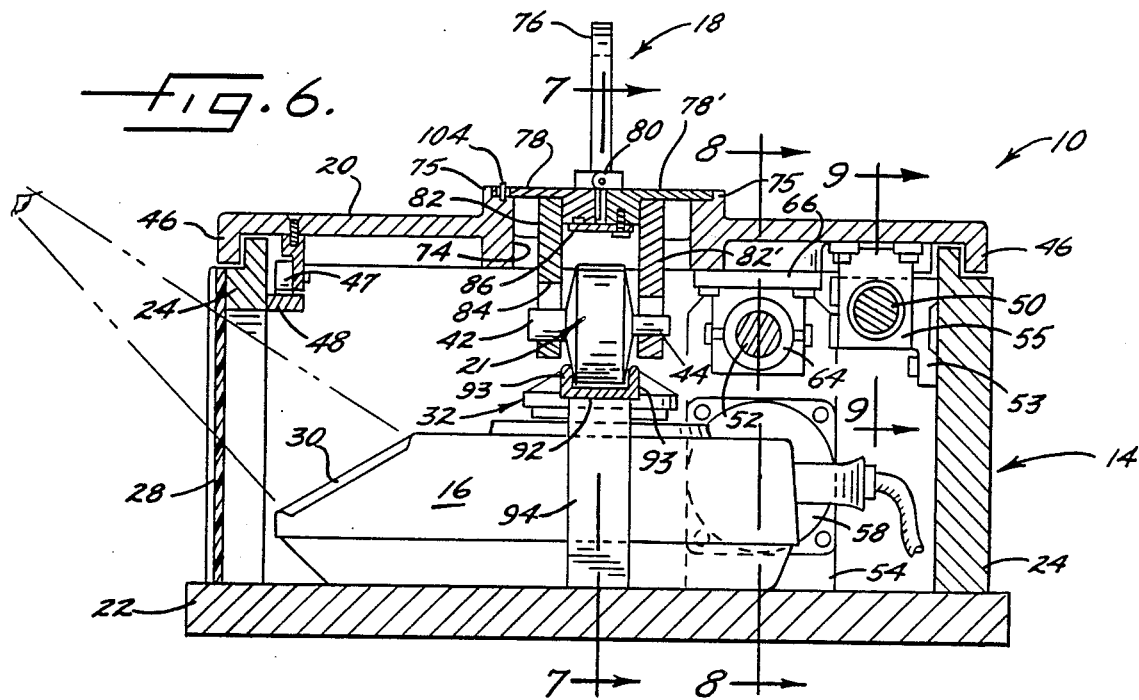
FIG. 6 is a transverse sectional view taken substantially along the line 6—6 through the apparatus of FIG. 1.

The apparatus 10 shown in FIG. 1 includes electronic control and recording means 12 connected to elongate housing means 14 containing weighing means illustratively consisting of seven identical weighing devices 16. Apparatus 10 also has article transporting means, which includes portable article support members 18, 18' and a carriage member 20, for conveying Cambridge pad units 21, or other articles to be weighed, to, longitudinally of, and from housing 14.

Housing 14 has a horizontal bottom wall 22 and upstanding side and end walls 24, 26. At least the front side wall and the end walls of housing 14 may be and illustratively are provided with removable viewing and access ports or windows 28 formed of glass or other transparent material.

Figure 7:
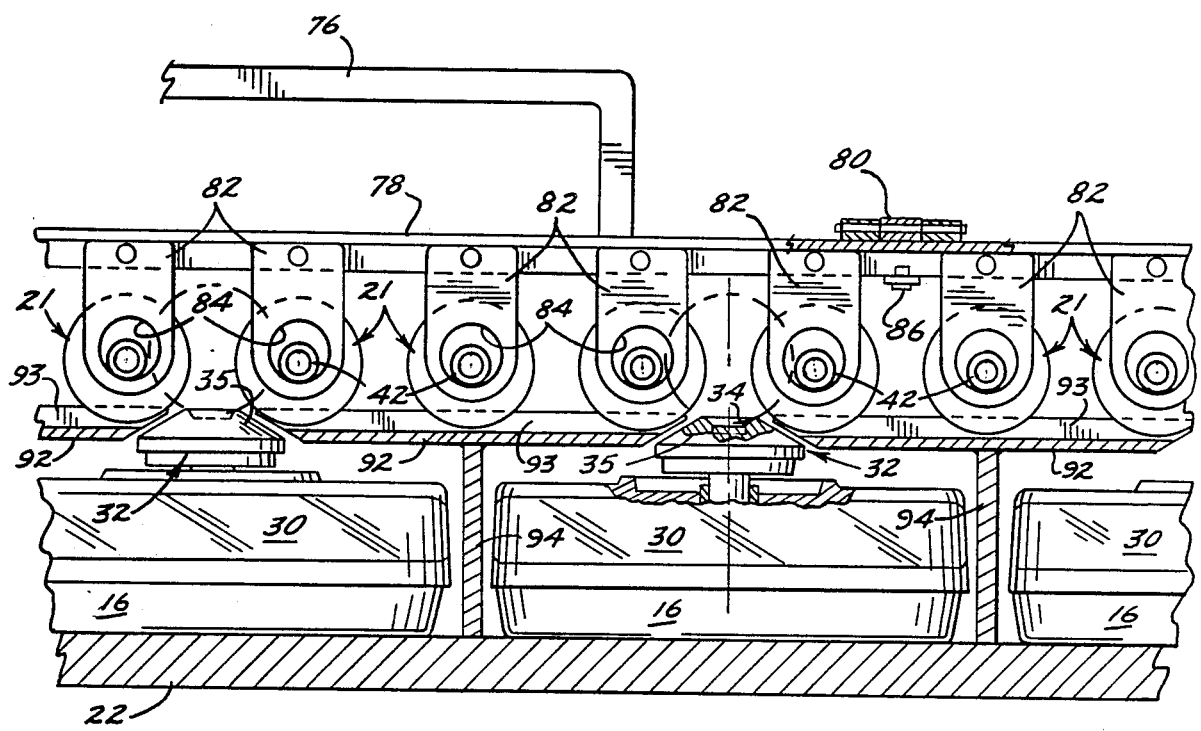
FIG. 7 is a fragmentary view, primarily in longitudinal sectional, but with some components being shown in elevation, taken substantially along the line 7—7 through the apparatus of FIG. 6.

Seven weighing devices 16 are mounted upon bottom wall 22 of housing 14 in laterally spaced adjacent relationship to each other, and collectively define an array that extends in linear fashion longitudinally of the housing. Each weighing device 16 is connected to control means 12 which, among other functions, controls the operation of the devices and electronically records the weight of each of the Cambridge pad units 21 weighed by them. Each weighing device 16 may and illustratively does also have a visual weight display panel 30 that is viewable, as indicated in FIG. 6, through the adjacent one of the windows 28 of the housing. Each weighing device 16 further includes a vertically movable weighing pan or platform member 32 that underlies and supports a Cambridge unit 21 during weighing thereof by device 16. As is best shown in FIGS. 2 and 7, each platform member 32 is of generally frusto-conical shape, and has an annular sloping cam surface 35 that encircles and slopes upwardly to a seat 34. Each seat 34 consists of a generally cylindrical recess that extends axially inwardly through the upper surface of member 32, and has a beveled upper edge. As is indicated in FIG. 2, seat 34 is adapted to receive and temporarily support the lower part of the generally disc-shaped main body 38 of a Cambridge unit 21 moved diametrically along the upwardly sloping surface of platform member 32 to seat 34. Unit 21 conventionally includes an interior filter pad (not shown), and tubular stem members 42, 44 of differing diameters that project axially outwardly from opposite sides of its main body 38. As is well known to those skilled in the art, when unit 21 is mounted within a smoking machine (not shown), one of its stems receives a cigarette to be tested, and the other stem is connected to a suitable intermittent vacuum source.

Movable carriage member 20 of apparatus 10 is mounted adjacent the top portion of housing 14 for movement longitudinally of the housing above and parallel to the array of weighing devices 16. The generally plate-like main body of carriage 20 has upon its opposite longitudinally extending edges downwardly extending flanges 46 (FIG. 6) that are in closely adjacent relationship to flanged upper end portions of housing side walls 24. The main body of carriage 20 is supported adjacent its forwardmost edge by thereto connected rollers 47, one of which is shown in FIG. 6, that are movable longitudinally of a track member 48 extending inwardly from the upper part of the front (leftmost, as viewed in FIG. 6) wall 24 of the housing. The rearward (right, as viewed in FIG. 6) section of the main body of carriage member 20 overlies a smooth-surfaced support shaft 50 and a rotatable threaded drive shaft 52. Referring now also to FIGS. 8 and 9, brackets 53, 54 connect shafts 50, 52 to walls of housing 14 and in parallel relationship to each other and to the central axis of housing 14. The one of brackets 54 shown in FIG. 8 also supports a reversible drive motor 58, preferably of the stepper type, whose output shaft 60 is connected by suitable pulleys 61 and a timing belt 62 to shaft 52. Carriage member 20 is supportively connected adjacent its opposite ends to shaft 50 by brackets 55 containing suitable bearings permitting relative longitudinal movement between the shafts and brackets An internally threaded traveling ball-nut or similar member 64 upon threaded shaft 52 is connected to the undersurface of carriage 20, as by a bracket 66. Rotation of shaft 52 by drive motor 58, which is under the control of control means 12, in one direction effects movement of member 64 and carriage 20 longitudinally of housing 14 toward one end thereof. Rotation of the shaft in the opposite direction similarly effects movement of carriage 20 toward the other end of the housing.

The opposite ends of carriage 20 are spaced inwardly from the ends of housing 14. In order to prevent drafts and the like from entering housing 14 via the end portions thereof not overlaid by carriage 20, extendable and retractable cover means 66 are mounted within the housing end portions. Referring to FIG. 8, which shows the left end of housing 14, each cover means 66 includes a band 68 of flexible fabric, plastic or similar cover material which is fixedly secured at one end to the adjacent end of carriage 20 and which extends therefrom about a spring biased supply roll 70. Movement of carriage 20 to the right lengthens the generally horizontal upper flight or expanse of the cover material 68 and unwinds additional material from the supply roll 70 at the left end of housing 14. Movement of carriage 20 in the opposite direction, i.e., to the left, shortens the upper flight of such cover material 68 and permits the spring-biased supply roll 70 to wind up additional quantities of the material in window-shade fashion. The cover means 66 in the opposite end portion of housing 14 operates in the same manner but of course takes up its cover material during rightward carriage movement and pays out the material upon leftward carriage movement. Material 68 therefore at all times covers the opposite end portions of housing 14, so as to prevent entry of drafts, dust and the like.

An elongate opening 74, which is bordered by an upstanding flange 75, extends through and centrally of carriage 20 along substantially the entire length thereof. Opening 74 and flange 75 are adapted to receive and releasably retain two identical Cambridge unit support members 18 (FIG. 1) in axially aligned relationship with each other and in parallel relationship to the common longitudinal axis of housing 14 and the array of weighing devices 16. As is best shown in FIGS. 3-5, each support member 18 has a carrying handle 76 secured to an elongate main body portion comprised of pivotally movable sections 78, 78' that are interconnected by hinges 80. At spaced locations along the length of member 18 a plurality of pairs of confronting support elements 82, 82' depend downwardly from sections 78, 78'. Elements 82, 82' have aligned openings 84, 84' respectively extending through their lower end portions. Each support member 18 also includes a latch 86 that when engaged secures the pivotally movable sections 78, 78' of the support member in their FIG. 4 closed condition. As is indicated in FIG. 5, disengagement of latch 86 permits relative pivotal movement of sections 78, 78' to an open position wherein Cambridge units 21 can be readily brought into and/or out of association with the support member. When units 21 are supported by a support member 18, the units are longitudinally aligned with and spaced from each other, and each pair of confronting support elements 82, 82' receives within their openings 84, 84' respective ones of the tubular stem elements 42, 44 projecting axially from opposite sides of the main body of a Cambridge unit. The opening 84 in each support element 82 that receives the larger diameter stem 42 of a Cambridge unit 21 may be and illustratively is larger than the opening 84' in the confronting support element 82' that receives the smaller diameter stem 44 of unit 21. When a group of Cambridge units 21 are supported solely by one of the support members 18, as shown in FIG. 3, the stem members 42, 44 of each Cambridge unit 21 extend substantially horizontally, and rest upon the bottom surfaces of the openings 84, 84' through which they respectively extend. The openings 84, 84' are sufficiently larger than the stem members 42, 44 received thereby as to permit free upward movement of each Cambridge unit 21 relative to elements 82, 82' when it is subjected to an upwardly directed force of sufficient magnitude.

Support members 18 may be and preferably are used to conveniently transport the therewith associated Cambridge units 21 between weighing apparatus 10 and some other location such as that occupied by a smoking machine (not shown) utilizing the units. Additionally, support members 18 are used to introduce Cambridge units 21 into housing 14 prior to weighing, to effect movement of the units with carriage 20 during weighing, and to thereafter remove the units from the housing. The units 21 carried by support members 18 are introduced into housing 14 simply by lowering the members downwardly toward carriage opening 74 until the peripheral edges of their sections 78, 78' are seated by the shouldered upper portion of the flange 75 bordering carriage opening 74. When so positioned, support members 18 are constrained against significant lateral and/or longitudinal movement relative to carriage member 20. The support elements 82, 82' of the seated support members 18 extend downwardly through carriage opening 74 into the interior of housing 14. Unless engaging weighing platform members 32, the elevation of units 21 is such that their lowermost surfaces are located in a common horizontal plane that extends through the sloping cam surfaces of members 32. A vertical plane containing the central axes of platform members 32 bisects units 21 and also guide rails 92 that are secured to housing 14 by vertical supports 94 and that extend longitudinally of the housing except in those areas occupied by the platform members. Cambridge units 21 carried by support members 18 overlie rails 92 but are not vertically supported by them. Upstanding side flanges 93 of the rails extend adjacent lower opposite side portions of the main bodies of the Cambridge units and limit lateral movement of the units to one side or the other of the vertical plane containing the central axes of weighing device platform members 32. The ends of rails 92 have a taper complementary to that of the sloping surfaces of members 32 so that the flanges of the rails continue to provide lateral guidance to the units during their longitudinal movement along, as well as between, members 32.

When the longitudinal positions of carriage 20, support members 18, and Cambridge units 21 are as shown in FIG. 7, none of the units engage members 32 of weighing devices 16. Longitudinal movement of the carriage and support members in either direction through one-half of the distance (which distance is hereinafter referred to as one step), between the centers of adjacent units 21 causes one of the units adjacent each member 32 to engage and move upwardly along the sloping cam surface of such member from its solid line position shown in FIG. 7 to a phantom-line position wherein the bottom of the unit's main body is received and supported by the seat 34 of the member 32. Due to the differences in diameter of the Cambridge unit stems 42, 44 and the support element openings 84, 84' through which the stems project, the upward movement of units relative to their associated support elements 82, 82' can and does occur freely and, when a unit reaches its seated phantom line position upon member 32, the entire weight of the unit is borne by such member. Further linear movement of carriage 20, in the same direction or in the opposite direction, disengages the seated Cambridge units from seats 34, and thereafter moves them out of engagement with members 32. When not supported by a member 32, each Cambridge unit is of course supported via its stems 42, 44 by a pair of the support elements 82, 82' and is constrained laterally by the upstanding flanges 93 of one of the guide rails 92.

Prior to commencement of a weighing operation by apparatus 10, the Cambridge units 21 to be weighed are transported to the apparatus by support members 18 from a smoking machine (not shown) or other source. The units 21 are introduced into housing 10 through opening 74 of carriage 20 as the main bodies of members 18 are lowered into supported engagement with the flange 75 surrounding such opening. While two support members 18 which each support a group of ten units 21 are shown, it will be appreciated that a single support member of different length might be employed to simultaneously transport all twenty units, or some other number of them. To insure consistent placement of members 18 in their proper orientations and positions upon carriage 74 during each weighing operation, vertical bores or other openings 102 are provided through edge portions of members 18 and mating pins or studs 104 are provided upon carriage flange 75, as shown in FIG. 1.

During placement of Cambridge units 21 into housing 14 the position of carriage 20, and thus of support members 18 and units 21, relative to weighing devices 16 are as schematically shown in FIG. 10 of the drawings. To facilitate description of a typical weighing operation, each of the Cambridge units 21 shown in FIG. 10 is further identified by the letter A, B or C. As indicated in FIG. 10, upon their initial insertion into housing 14, none of the Cambridge units 21 overlie or engage any of the platform members 32 of weighing devices 16. Operator actuation of a "start" button or switch 96 (FIG. 11) associated with the apparatus control means 12 initiates a weighing operation. During such weighing operation, control means 12 automatically causes carriage 20 to undergo a series of longitudinal movements. These carriage movements effect movement of Cambridge units 21 in substantial unison with each other to a plurality of different locations longitudinally of housing 14 and the linear array of weighing devices 16. At each of such locations a plurality but less than all of the Cambridge units are weighed substantially simultaneously by underlying associated ones of weighing devices 16, and their weights are automatically recorded by control means 12. The control means may and preferably does further tare the weight when the Cambridge units 21 being weighed are ones which have been removed from the smoking machine and whose filters contain "FTC tar," so as to give the net weight of such material. The units 21 weighed at each location are separated from each other by at least one, and illustratively by two, units 21 which are not weighed at that location. Additionally, since the units 21 weighed at each location have been displaced upwardly by their engagement with the sloping cam surfaces of the underlying platform members 32, such units are disposed at a higher elevation than the other units while being weighed.

The sequential movements undergone by support members 18 and Cambridge units 21 during a typical weighing operation are illustrated in FIGS. 10A–10D of the drawings. As is apparent from comparison of FIGS. 10 and 10A, after being introduced into housing 14, the support members and Cambridge units 21 are first moved one-half of a step to the right to a first location wherein each of the seven Cambridge units 21 that are further designated by the letter A are supported and weighed by the underlying weighing platforms 32 of respective underlying ones of the weighing devices 16. Support members 18 and units 21 next undergo a full step of longitudinal movement to their FIG. 10B location. In this location, each of the seven mutually spaced Cambridge units 21 that are further identified in FIGS. 10 and 10B by the letter B are supported and weighed by underlying respective ones of weighing devices 16. Support members 18 and Cambridge units 21 are next moved another full step to the right to their longitudinal location shown in FIG. 10C, wherein the remaining "C" units 21 are supported and weighed by respective underlying ones of weighing devices 16. Since there are only six of these remaining units 21 to be weighed, the leftmost (as viewed in FIG. 10C) one of the weighing devices 16 is inactive during this phase of the weighing operation. Prior to removal of support members 18 and units 21 from apparatus 10, carriage 20 preferably is moved one more time to a location, such as that shown in FIG. 10D or FIG. 10, wherein none of the units 21 engage weighing devices 16. This helps prevent damage to the weighing devices during removal of support members 18 and units 21 from housing 14 of apparatus 10.

In addition to performing the above-noted functions of effecting the desired sequential movements of carriage 20, controlling operation of weighing devices 16, and recording the weights of units 21, control means 12 may further automatically monitor the status of each weighing operation and report any errors that might occur during weighing. Additionally, the control means may include a bar code reader or similar device 98 (FIG. 11) that during each weighing operation scans identifying indicia (not shown) upon support members 18 and/or Cambridge units 21, and transmits data indicative thereof to the computer 100 of the control means.

The automatic weighing system of the present invention rapidly and accurately provides the desired weight data, and is relatively inexpensive, both in relation to the cost of a purely manual system, and in relation to the cost of a system in which the number of weighing devices is the same as the number of Cambridge units or other articles to be weighed during each weighing operation.

While specific embodiments of the method and apparatus of the invention have been shown and described, this was for purposes of illustration only, and not for purposes of limitation, the scope of the invention being in accordance with the following claims.

We claim:

1. Apparatus for weighing Cambridge units used in cigarette testing and each having a generally disc-like main body and tubular stems projecting outwardly from opposite sides of said body, comprising:
   an elongate housing;
   an array of weighing devices mounted within and extending longitudinally of said housing;
   transporting means for supporting a group of said units within said housing and for transporting said units in unison with each other longitudinally of said array of weighing devices between different locations in each of which different ones of said units are supportively engaged and weighed by said weighing devices.

2. Apparatus as in claim 1, wherein said transporting means includes a carriage, means mounting said carriage upon said housing for bi-directional movement longitudinally of said array of weighing devices, and reversible drive means connected to said carriage for imparting said bi-directional movement to said carriage.

3. Apparatus as in claim 2, wherein said transporting means further includes support means removably associated with said carriage for transporting said units to and from said housing, and for effecting movement of said units in unison with each other and said carriage longitudinally of said array.

4. Apparatus as in claim 3, wherein said support means includes a plurality of support elements supporting said units for said movement longitudinally of said array, and for limited vertical movement relative to said support means and to weighing devices of said array.

5. Apparatus as in claim 4, wherein each of said units is releasably supported by a pair of said support elements, and said support elements each have an opening therein adapted to receive a therewith associated one of said stems of said unit.

6. Apparatus as in claim 5, wherein said stems of each of said units are of different diameter and said openings of each of said pairs of said support elements are of different sizes.

7. Apparatus as in claim 1, wherein each of said weighing devices includes a weighing platform having a seat adapted to receive one of said units.

8. Apparatus as in claim 7, wherein each of said weighing platforms of said devices has a sloping surface adapted to direct ones of said units moving along said surface toward said seat of said unit.

9. Apparatus as in claim 8, wherein said weighing platform of each of said devices has an upwardly opening recess therein, and said seat includes said recess.

10. Apparatus as in claim 9, wherein said recess of each of said platforms has a beveled upper edge, and said housing substantially totally encloses said weighing devices and shields said devices from drafts during operation of said apparatus.

11. Apparatus as in claim 1, and further including guide means carried by said housing for restraining lateral movement of said units while permitting longitudinal and vertical movement thereof relative to said array.

12. Apparatus as in claim 11, wherein said guide means includes a plurality of flanged guide rails extending longitudinally of said array of weighing devices.

13. Apparatus as in claim 12, wherein said guide rails have beveled ends in spaced adjacent relationship to each of said platforms of said weighing devices.

14. Apparatus for weighing articles, comprising:
   a plurality of weighing devices located in spaced relationship to each other and defining an array;
   transporting means for moving a group of said articles in unison with each other generally parallel to said array between successive different locations at each of which a plurality of different ones but not all of said articles of said group are received and weighed substantially simultaneously by underlying associated ones of said weighing devices, said articles weighed at each of said locations being separated from each other by other articles of said group.

15. Apparatus as in claim 14, wherein the number of said weighing devices in said array is less than the number of said articles in said group.

16. Apparatus as in claim 14, wherein said array of said devices and said group of said articles are each approximately linear, and said transporting means is located above said array of said weighing devices.

17. Apparatus as in claim 14, and further including an elongate housing, said weighing devices being mounted by and within said housing at spaced locations along the length thereof, said transporting means including a carriage mounted by said housing for movement longitudinally thereof above and relative to said weighing devices, and drive means for imparting said movement to said carriage.

18. Apparatus as in claim 17, wherein said transporting means further includes portable article support means for transporting said group of said articles from a distal site to said apparatus, and means for mounting said article support means within said carriage member for movement of said article support means and said articles in unison with said carriage member longitudinally of said housing.

19. Apparatus as in claim 17, and further including guide means within said housing for restraining lateral movement of said articles during said movement thereof with said carriage longitudinally of said housing.

20. Apparatus for weighing articles, comprising:
a plurality of weighing devices located in spaced relationship to each other and defining an array;
transporting means for moving a group of said articles in unison with each other generally parallel to said array between successive different locations at each of which a plurality of different ones but not all of said articles of said group are received and weighed substantially simultaneously by underlying associated ones of said weighing devices; each of said weighing devices including an article receiving weighing platform having cam surface means for engaging different ones of said articles during movement thereof by said transporting means, and for directing thereby engaged ones of said articles to a preselected location upon said platform.

21. Apparatus as in claim 20, wherein said array of said devices and said group of said articles are each approximately linear, and said transporting means is located above said array of said weighing devices.

22. Apparatus as in claim 20, and further including an elongate housing, said weighing devices being mounted by and within said housing at spaced locations along the length thereof, said transporting means including a carriage mounted by said housing for movement longitudinally thereof above and relative to said weighing devices, and drive means for imparting said movement to said carriage.

23. Apparatus as in claim 20, wherein said transporting means includes portable article support means for transporting said group of said articles from a distal site to said apparatus.

24. Apparatus as in claim 22, and further including guide means within said housing for restraining lateral movement of said articles during said movement thereof with said carriage longitudinally of said housing.

25. A method of weighing articles using a plurality of weighing devices mounted in spaced relationship to each other and defining an array, comprising:
transporting the articles parallel to the array in substantial unison with each other to successive different locations while supporting and weighing different ones of the articles at each of the locations by underlying ones of the weighing devices.

26. A method as in claim 25, wherein the array of weighing devices is substantially linear, and the transporting of the articles is along a path extending above and substantially parallel to the array.

27. A method as in claim 25, and further including, prior to the transporting of the articles, mounting the articles upon an article support at a site distal from the array, and moving the support and the articles mounted thereon in unison with each other from the distal site to the array; and wherein the step of transporting the articles includes transporting the article support in unison with the articles relative to the array.

28. A method as in claim 25, and further including constraining movement of the articles laterally of the array during the transporting thereof.

29. A method as in claim 25, and further including effecting relative vertical movement between articles weighed at each of the locations and other of the articles.

30. A method as in claim 29, wherein the step of effecting relative vertical movement includes effecting engagement of the article weighed at each of the locations with sloping cam surfaces.

* * * * *